United States Patent [19]

Ziegenhain

[11] 4,267,161
[45] May 12, 1981

[54] METHOD OF MAKING ALUMINUM CHLOROHYDRATE

[75] Inventor: William C. Ziegenhain, Ponca City, Okla.

[73] Assignee: Conoco, Inc., Ponca City, Okla.

[21] Appl. No.: 142,587

[22] Filed: Apr. 21, 1980

[51] Int. Cl.$^3$ ............................ C01F 7/56; C01F 7/02
[52] U.S. Cl. .................................. 423/462; 423/472; 423/625; 423/630; 264/63; 264/65; 264/DIG. 19
[58] Field of Search ...................... 423/462, 472, 630; 260/448 AC; 264/176 F, DIG. 19, 63

[56] References Cited

U.S. PATENT DOCUMENTS

| | | | |
|---|---|---|---|
| 2,975,201 | 3/1961 | Dickey | 260/448 R |
| 3,865,917 | 2/1975 | Galasso | 264/63 |
| 3,887,691 | 6/1975 | Kobetz | 423/462 |

FOREIGN PATENT DOCUMENTS

| | | | |
|---|---|---|---|
| 1947177 | 4/1971 | Fed. Rep. of Germany | 260/448 AC |
| 1414854 | 11/1975 | United Kingdom | 264/63 |

*Primary Examiner*—Brian E. Hearn
*Attorney, Agent, or Firm*—Cortlan R. Schupbach, Jr.

[57] ABSTRACT

Aluminum chlorohydrate is prepared by a method comprising (a) forming aluminum methoxide from aluminum alkoxides using methanol;
(b) recovering aluminum methoxide as a solid precipitate phase, washing to remove higher alcohols and drying to recover a powder;
(c) reacting the recovered powdered aluminum methoxide with dilute hydrochloric acid to form aluminum chlorohydrate.

8 Claims, No Drawings

METHOD OF MAKING ALUMINUM CHLOROHYDRATE

This invention relates to a method for producing alumina fibers. More specifically, this invention relates to a method for producing alumina fibers by a unique method of forming aluminum chlorohydrate then drawing the aluminum chlorohydrate into alumina fibers.

The making of inorganic ceramic fibers comprising metal oxides is well known in the art. U.S. Pat. No. 3,865,917 shows a method of making alumina monofiliments by extruding a 50 to 60 weight percent aqueous solution of aluminum chlorohydrate. U.S. Pat. No. 3,887,691 shows methods for making hydroxy chloroaluminum compounds. British Pat. No. 1,414,854 shows a method for preparing alumina yarns by using hydroxy chloro aluminum compounds. U.S. Pat. No. 3,950,478 discloses a method for spinning alumina fibers which contain an organic polymer. British Pat. No. 1,470,292 teaches the production of inorganic fibers using polyethylene oxide and alumina combinations.

However, these methods deal with aluminum chlorohydrate or organic-containing aluminum compounds which are then spun into fibers. Previous methods for obtaining aluminum chlorohydrate have been inefficient and produce aluminum chlorohydrate which contains contaminants. U.S. Pat. No. 4,024,231 shows the water hydrolysis of aluminum methoxide in anhydrous methanol. The reference is directed toward a process for preparing alumina and produces an aluminum methoxide which did not react with alcohol. U.S. Pat. No. 2,975,201 describes the preparation of aluminum methoxide by the transalcoholysis of a Ziegler organoaluminum chemistry growth product with methanol. However, this growth product was not treated with acid to form aluminum chlorohydrate solutions suitable to form fibers as described in the instant invention. Aluminum chlorohydrate is thus usually made by reacting aluminum metal with aqueous hydrochloric acid.

U.S. Pat. No. 3,887,691 describes the preparation of oxychlorides from alkoxides having a carbon atom content of from 6 to 30 carbon atoms. The patent describes aluminum alkoxides preferably having alkoxy groups whose corresponding alcohols are substantially insoluble in water. This reference uses an aqueous acid and produces higher alcohols. However these higher alcohols tend to remain trapped in the product and alter the properties of the aluminum chlorohydrate solution. The reference likewise develops two immiscible liquid phases which require much separation and careful handling prior to obtaining the product.

It would therefore be of great benefit to provide a method wherein aluminum chlorohydrate could be produced in an easily recoverable form using a simple process containing few by-products.

It is therefore an object of the present invention to provide an improved method for obtaining aluminum chlorohydrate. It is a further object to provide a method for obtaining alumina fibers. Other objects will become apparent to those skilled in this art as the description proceeds.

It has now been discovered according to the present invention that aluminum chlorohydrate can be obtained by a method comprising (a) reacting aluminum alkoxides with methanol at a temperature of from about 130° F. to about 450° F. for a time sufficient to form solid aluminum methoxide in a liquid phase, (b) washing the obtained aluminum methoxide to remove higher alcohols and recovering solid aluminum methoxide from the liquid phase, and (c) reacting aluminum methoxide with hydrochloric acid for a time and at a temperature sufficient to form aluminum chlorohydrate.

In accordance with the present invention, it has been found that only methanol is effective in forming a solid precipitate material which can be recovered by simple filtration and which is suitable for use in alumina fiber. Although some methanol is present in these fibers, it is easily removed because of its low volatility. The presence of higher molecular weight alkanols and fibers produced by other processes makes such alcohols difficult to remove and degrades the properties of the fibers. This is not true in the method of the instant invention. The instant invention does not require aluminum metal as a feedstock, although aluminum metal can be used. The aluminum chlorohydrate produced will have the formula $Al_2(OH)_xCl_y$, where X is any number from 1–5 and y is 6–X.

Normally step (c) is carried out at reflux temperature of the solution for a time sufficient to react substantially all washed aluminum methoxide to form water soluble aluminum chlorohydrate. The hydrochloric acid (HCl) used in step (c) is a dilute aqueous solution usually containing from about 2 to about 30 weight percent HCl. Use in this range is not critical, but higher concentrations of HCl decrease the effectiveness of the present invention.

The aluminum alkoxides of step (a) can be any aluminum alkoxide from any source which contains from about 2 to about 30 carbon atoms. However, in most commercial applications the aluminum alkoxides obtained will contain from about 6 to about 18 carbon atoms, with the majority of the alkoxide in the range of from about 10 to about 18 carbon atoms.

In carrying out the method of the present invention, normally the recovered solid aluminum methoxide of step (b) is washed with methanol to remove any higher alcohols present by displacement then dried to remove methanol prior to reaction with HCl. The recovery of the solid of step (b) can be made by any method convenient such as filtration or centrifugation.

The reaction of the aluminum alkoxides with methanol is normally carried out at a temperature of from about 130° F. to about 450° F. Preferred temperature range is from about 150° F. to about 350° F. but from about 325° F. to about 375° F. is most preferred.

In addition, the reaction of aluminum alkoxides of step (a) can optionally be carried out in a liquid phase under pressure, although this is not critical to the present invention. The reaction under pressure is simply faster and is therefore a preferred method of carrying out the present invention.

Once the aluminum chlorohydrate has been recovered as an aqueous solution with methanol, the aluminum chlorohydrate is concentrated by removing methanol and sufficient water to form a solution of sufficient viscosity suitable for drawing fibers. Fibers are then drawn from the concentrated solution. Methods for drawing fibers suitable for use in the process of the present invention are those well known to those skilled in the art and are exemplified by the procedures set forth in U.S. Pat. No. 3,865,917; U.S. Pat. No. 3,887,691;

British Pat. No. 1,414,854; and French Pat. No. 2,176,041.

In particular, a suitable process for producing alumina fibers can be found in U.S. Pat. No. 3,950,478, hereby incorporated by reference in its entirety into the instant specification. As set forth in this reference, organic polymers can be added to the viscous aluminum chlorohydrate mixture to aid in drawing fibers and enhance fiber formation. These organic polymers are preferably water soluble organic polymers; conveniently a non-ionic water soluble organic polymer, polyhydroxylated organic polymers or natural water soluble gums. These polymers are preferably thermally stable under the conditions of drawing the fiber. Examples of preferred organic polymers include polyvinyl alcohol, polyacralamid, partially hydrolyzed polyacrylamide, polyacrilic acids, polyethylene oxides, carboxyalkyl celluloses, hydroxyalkyl celluloses, alkyl celluloses, hydrolyzed starches, dextrans, quargum, polyvinylpyrrolidones, polyethylene glycol, alginic acids, polyisobutylene derivatives, copolymers of polycyloxanes such as with ethylene oxide, polyurethanes and esters and ester copolymers.

The most preferred organic polymers useful in drawing fibers are straight chain polyhydroxylated organic polymers such as polyvinyl alcohol, polyvinylpyrrolidone or polyethylene oxide.

The viscosity of the drawing composition is preferably less than 300 poise most preferably from 0.1 to 100 poise, especially when very small diameter fibers are to be drawn.

The use of elevated temperatures increases the reaction rate, together with selectivity to $Al(OCH_3)_3$. At room temperature the methanol and alkoxide form a gel-like reaction product. Phase separation is not possible with this product unless large excesses of methanol are used.

The invention is more concretely described with reference to the examples below wherein all parts and percentage are by weight unless otherwise specified. The examples are provided to illustrate the instant invention and not to limit it.

EXAMPLE 1

A 10 gallon Pfaudler mixer (trademark of and sold by Pfaudler Co., Division of Sybron Corp, Rochester, N.Y.) was charged with 9486 grams of reagent grade methanol to which was added 1770 grams of aluminum alkoxides obtained from a commercial Ziegler growth process. The contents of the reactor were heated to 200° F. and maintained at this temperature for 2 hours. The internal pressure ranged from 30 to 32 pounds per square inch gauge (psig). The reactor was then cooled to 160° F. and filtering was begun. An aluminum methoxide solid weighing about 1160 grams was recovered leaving about 400 grams of solids in the Pfaulder as a holdup. The total crude alcohol filtrate recovered was 9667 grams.

The filtercake solids from the aluminum methoxide produced weighed 1151 grams and were recharged to the Pfaulder after the mixer was cleaned. Fresh analytical reagent grade methanol (9455 grams) was added to the mixer. The materials were mixed and reheated to 198° F. for 30 minutes with the pressure holding at about 30 psig. The reactor contents were then cooled to 183° F. and filtration was begun. Filtration used Whatman No. 5 filter paper and collected 9530 grams of filtrate and 1095 grams of solid.

Once the rewash was complete, drying of the filtercake was carried out by charging 1095 grams of wet filtercake to a vacuum flask in a hot water bath. The pressure in the flask was slowly lowered until methanol was distilled overhead at 14.3 inches mercury pressure. The cold water condenser was used to recover the methanol condensate. Over a 4 hour period the vacuum was slowly increased to 26.5 inches of mercury at 85° to 90° C. to complete drying of the aluminum methoxide. The process yielded 512 grams of dried powder containing 68.3 weight percent aluminum methoxide, with the remainder mostly methanol which had not been removed during the drying procedure.

The aluminum methoxide was converted to aluminum chlorohydrate by mixing 60 grams of concentrated acid (37% HCL) into 200 grams deionized water which was charged to a 2 liter, 3 neck distillation flask, and fitted with mixer and water cool condenser. The flask and its contents were heated to 80° C. and 200 grams of dried aluminum methoxide powder containing 68.3 weight percent aluminum methoxide was added slowly over a 10 minute period. The contents of the flask were allowed to digest at the boiling point for 18 hours. It was noted that the boiling point temperature declined as methanol was released from the reaction. The reaction occurred mainly at about 150° F. The reactor contents were cooled and 402 grams of viscous liquid were recovered which were then filtered through No. 2 Whatman filter paper to remove inert solids. The filtrate was then heated under 26 inches of mercury vacuum at 85° C. in water solution for a period of time sufficient to concentrate the product at 230.4 grams the final product. The density of the final concentrate was 1.252 grams per cubic centimeter with an aluminum content of 10.38 weight percent and a chlorine content of 8.68 weight percent. Calculated mole ratio of aluminum to chlorine was 1.45/1.0.

EXAMPLE 2

Concentrated aqueous solutions of the reaction product resulting from example 1 (aluminum chlorohydroxide) were tested for fiber formation by attempting to pull fibers in the laboratory using a glass rod. The glass rod was simply touched to the solution and withdrawn slowly. Fibers could be drawn without additives, but fiber formation was enhanced by the addition of 1-2 percent of a high molecular weight polyvinyl alcohol.

Thus it is apparent that the instant invention provides an improved process for the production of aluminum chlorohydrates suitable for forming alumina fibers. The process utilizes the formation of aluminum methoxides which separates from the liquid as a solid and is easily recoverable. The recovered solid is easily converted to aluminum chlorohydrate suitable for forming fibers. Problems of undesirable by-products in critical separation by the prior art processes are avoided.

While certain embodiments and details have been shown for the purpose of illustrating this invention, it will be apparent to those skilled in this art that various changes and modifications may be made herein without departing from the spirit or scope of the invention.

I claim:

1. A method for preparing aluminum chlorohydrate comprising
   (a) reacting aluminum alkoxides with methanol at a temperature of from about 130° F. to about 450° C. for a time sufficient to form solid aluminum methoxide in a liquid phase, (b) washing the aluminum methoxide recovered with methanol to remove higher alcohols, then recovering solid aluminum methoxides from the liquid phase, and (c) reacting aluminum methoxide with aqueous hydrochloric acid for a time and at a temperature sufficient to form aluminum chlorohydrate.

2. A method as described in claim 1 wherein step (c) is carried out at reflux temperature for a time sufficient to react substantially all wash aluminum methoxide to form water soluble aluminum chlorohydrate.

3. A method as described in claim 2 wherein the hydrochloric acid is in a dilute aqueous solution containing from about 2 to about 30 weight percent hydrochloric acid.

4. A method as described in claim 3 wherein the aluminum alkoxide contains from 2 to 30 carbon atoms.

5. A method as described in claim 4 wherein the aluminum alkoxide contains from about 6 to 18 carbon atoms.

6. A method as described in claim 5 wherein the recovered solid of step (b) is washed with methanol to remove higher alcohols then dried prior to reaction with hydrochloric acid.

7. A method as described in claim 6 wherein the recovery of solids from step (b) is carried out by filtration or centrifugation.

8. A method as described in claim 7 wherein the reaction of step (a) is carried out at a temperature of from about 325° F. to about 375° F.

* * * * *